(12) United States Patent
Iinuma et al.

(10) Patent No.: US 6,549,609 B1
(45) Date of Patent: Apr. 15, 2003

(54) X-RAY GENERATOR WITH A LIMITING DEVICE

(75) Inventors: Masao Iinuma, Osaka (JP); Hajime Takemoto, Saitama (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/669,666

(22) Filed: Sep. 26, 2000

(30) Foreign Application Priority Data

Oct. 13, 1999 (JP) .......................................... 11-290370

(51) Int. Cl.7 ................................................. G21K 1/00
(52) U.S. Cl. ....................................... 378/150; 378/98.8
(58) Field of Search ............................... 378/98.7, 98.8, 378/145, 150, 151, 160, 205, 98.5

(56) References Cited

U.S. PATENT DOCUMENTS

| 4,490,835 A | | 12/1984 | Wons ........................ 378/146 |
| 5,142,559 A | * | 8/1992 | Wielopolski et al. ....... 378/205 |
| 5,539,798 A | * | 7/1996 | Asahina et al. ............ 378/98.5 |
| 6,243,441 B1 | * | 6/2001 | Zur ........................... 378/98.8 |

FOREIGN PATENT DOCUMENTS

FR    2 700 259    7/1994

OTHER PUBLICATIONS

Christensen's Physics of Diagnostic Radiology, Thomas S. Curry, James E. Dowdey, and Robert C. Murray, Jr., Lippincott Williams and Wilkins, 4th Edition, Chapter 18, pp. 266–288.*

* cited by examiner

*Primary Examiner*—Drew A. Dunn
*Assistant Examiner*—Therese Barber
(74) *Attorney, Agent, or Firm*—Rader, Fishman & Grauer PLLC

(57) ABSTRACT

An X-ray tube (3) is rotated about its focal point along a plane perpendicular to a body axis of a patient by an X-ray tube rotation driver and thus the X-ray irradiation field moves. When the side of the X-ray irradiation field reaches an edge detector (6a) in the edge part of the flat panel detector, the edge detector detects X-ray and provides a signal to a controller. The controller controls the X-ray limiting device (4a) to move shield blades thereof to limit the range of the X-ray irradiation field. The above structure makes it possible to move the center of the X-ray irradiation field without moving the patient and also to prevent the X-ray irradiation field from going outside of the flat panel detector.

15 Claims, 8 Drawing Sheets

X-RAY GENERATOR WITH A LIMITING DEVICE

BACKGROUND OF THE INVENTION

This invention is related to an X-ray apparatus for diagnosis of patients.

An X-ray apparatus has an X-ray limiting device, adjusting an X-ray irradiation field, attached to an aperture, for irradiating X-rays, of an X-ray tube. This X-ray limiting device makes it possible to reduce X-ray exposure dose of a person and also to enhance an X-ray image.

In this X-ray apparatus, an X-ray limiting device 4 is attached to an aperture, for irradiating X-rays, of an X-ray tube 3 which is held to a supporting arm 35, as shown in FIG. 7. An image intensifier 5 is attached below the table 1 upon which rests a person 2 for examination. The whole structures, including the supporting arm 35, the image intensifier 5, and so on, are supported by a supporting base 36.

As shown in FIG. 7, the X-ray limiting device 4 has two stages of blades which consist of lower blades 7, 8 and upper blades 9, 10. The lower blades 7 and 8 limit X-rays in the right and left directions, facing the FIG. 7. The upper blades 9 and 10 limit X-rays in the front and back directions, facing the FIG. 7. X-rays generated at an X-ray focal point 3a are limited by these blades 7, 8, 9, and 10 to form an X-ray flux 19 and then are irradiated onto the target part of the person 2.

When imaging the left part of the person 2, the table 1 is moved in the direction shown as the arrow A until the center of the imaging part of the image intensifier 5 and the center of an X-ray irradiation field reach the target part of the left part, and then imaging of the target part is carried out. When imaging the right part of the person 2, the table 1 is moved in the direction along the arrow B until the center of the imaging part of the image intensifier 5 and the center of an X-ray irradiation field reach the target part of the left part, and then imaging of the target part is carried out.

The following is a description of a structure of the X-ray limiting device 4, with reference of FIG. 8. The lower blades 7, 8, formed mainly of laden boards, are disposed in a case 25 and limit X-ray flux 19 to form a necessary and sufficient X-ray irradiation field. The lower blades 7, 8 are driven in a circular movement by a gear and link structure, or in a parallel movement by wire ropes, pulleys, and shafts disposed in parallel. The former allows for a simple structure. The other one makes it possible to limit an X-ray irradiation field accurately.

The upper blades 9, 10 and back blades (not illustrated) are also driven, engaging with the lower blades 7, 8. A small motor can be used to drive these blades. The upper blades 9, 10 greatly contribute to reduction of scattered radiation and leakage dose. The back blades efficiently reduce X-rays generated from the part other than the focal point 3a. The total performance of these three pairs of blades depends on their assembly dimensional accuracy and geometric relation to one another, as well as the performance of each blade.

The X-ray irradiation field is confirmed in a manner of visual observation of an optical irradiation field shown on the person 2. The optical irradiation field is formed by light, from a projector 13, reflecting on the mirrors 14, 15 and then going by the lower blades 7, 8. The X-ray irradiation field is also confirmed in a manner of visual observation of a needle 16 which moves, along a scale board 17, engaging with the lower blades 7, 8. These indicators make it possible to confirm the X-ray irradiation field without irradiating X-rays actually. Some of the prior art X-ray limiting devices do not have projector 13. A detachable filter 18 for controlling an amount of the total leakage which regulates X-ray quality is also usually provided with the X-ray limiting device 4.

In the conventional X-ray apparatus, constructed as described above, an imaging part which has the X-ray tube 3, the image intensifier 5, a snap shot device, not shown in the Figures, and so on, is fixed not to move along the width of the person 2, through the supporting arm 35. Thus, it is necessary to move the table 1 for changing an imaging area along the width of the person 2. When an examination with a brouchoscope, endoscope, and so on is also carried out, with the hardware inserted into the person being examined, this results in a heavy burden on the person 2. Also when an examination, making an X-ray irradiation field smaller with the X-ray limiting device 4 than the field of view of the image intensifier 5 for the purpose of reducing useless exposure, is carried out, the same problem occurs when changing an imaging area along the width of the person 2.

SUMMARY OF THE INVENTION

It is, therefore, an object of this invention to provide an X-ray apparatus which makes it possible to change an imaging area along the width of the person 2, for example, without burdening the person 2 in an examination with a brouchoscope, endoscope, and so on.

An X-ray apparatus of this invention has an X-ray tube, a solid state flat detector opposing said X-ray tube across a person for examination, an X-ray limiting device for limiting the X-rays from said X-ray tube, and a driver for rotating said X-ray tube and said X-ray limiting device along a plane which is perpendicular to the body axis of the person.

The X-ray apparatus also has an edge detector for detecting X-ray irradiated onto an edge part of the solid state flat detector, a controller for receiving a signal from the edge detector and controlling, with the signal, the X-ray limiting device so that X-rays do not come outside of the solid state flat detector.

In the X-ray apparatus, the edge detector consists of X-ray semiconductor elements in edge parts on the solid state flat detector.

In the X-ray apparatus, the edge detector may also consist of a separate X-ray detector from the solid state flat detector.

The X-ray apparatus also has a handle for providing signals depending on an amount set by an operator, and an X-ray tube rotation controller for rotating the X-ray tube depending on the signals.

The X-ray apparatus also has two handles for providing signals based on amounts set by an operator, and a shield blade movement controller for moving the two shield blades independently, depending on the signals.

The X-ray apparatus also has a detector for detecting a rotation angle of the X-ray tube, and providing signals related to the rotation angle, a controller for receiving the signals from the detector and controlling the X-ray limiting device so that X-rays from the X-ray tube do not go outside of the solid state flat detector.

DESCRIPTION OF THE PREFERRED EMBODIMENTS

Figure 1:
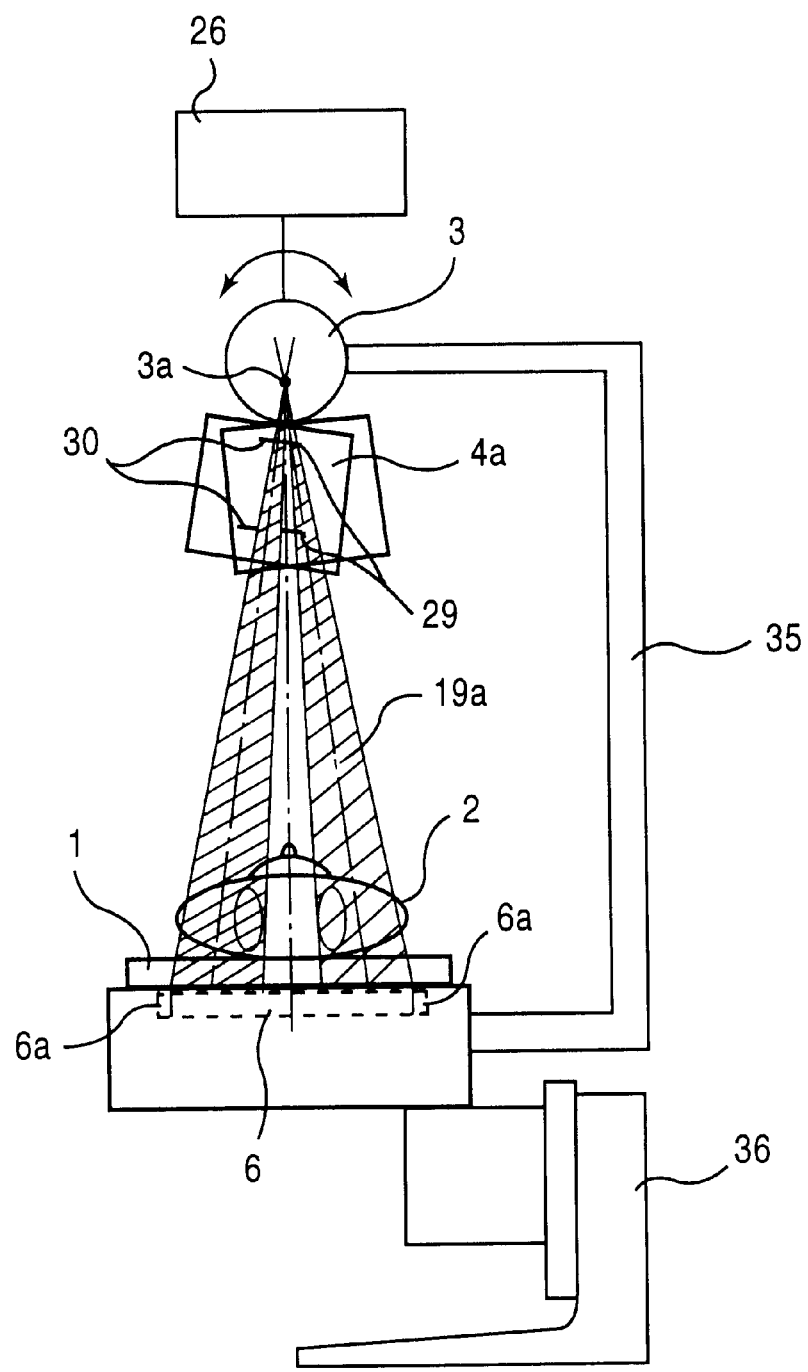
FIG. 1 is a schematic view of an X-ray apparatus in an embodiment of this invention.
Figure 2:
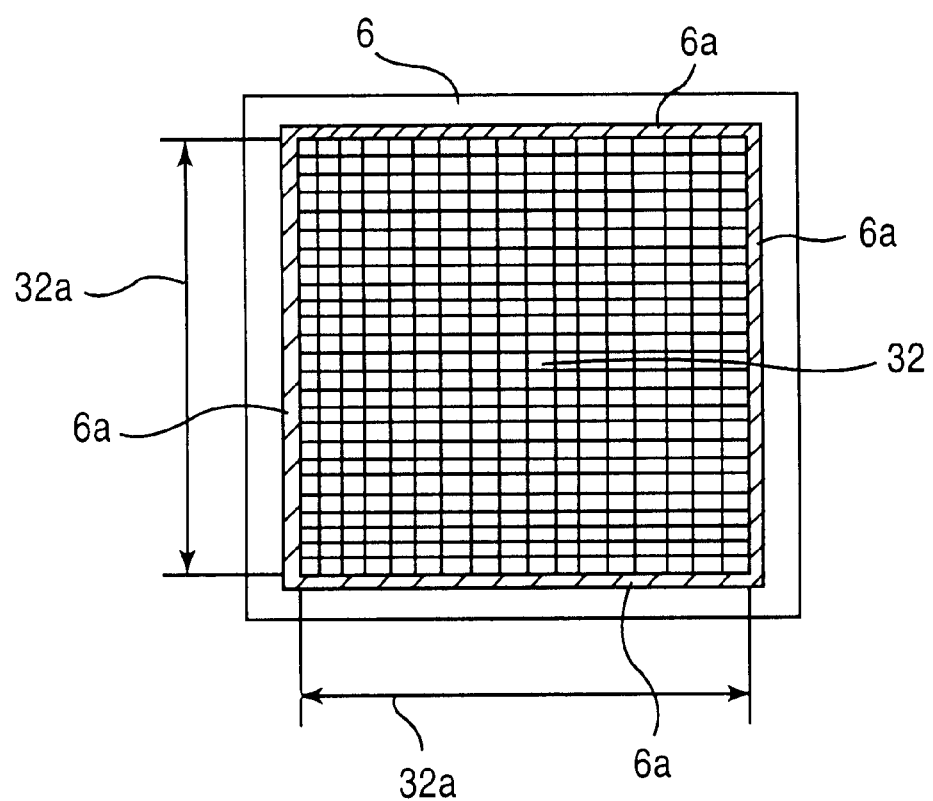
FIG. 2 is a schematic view of a solid state flat plate detector used for an X-ray apparatus in the embodiment of this invention.
Figure 3:
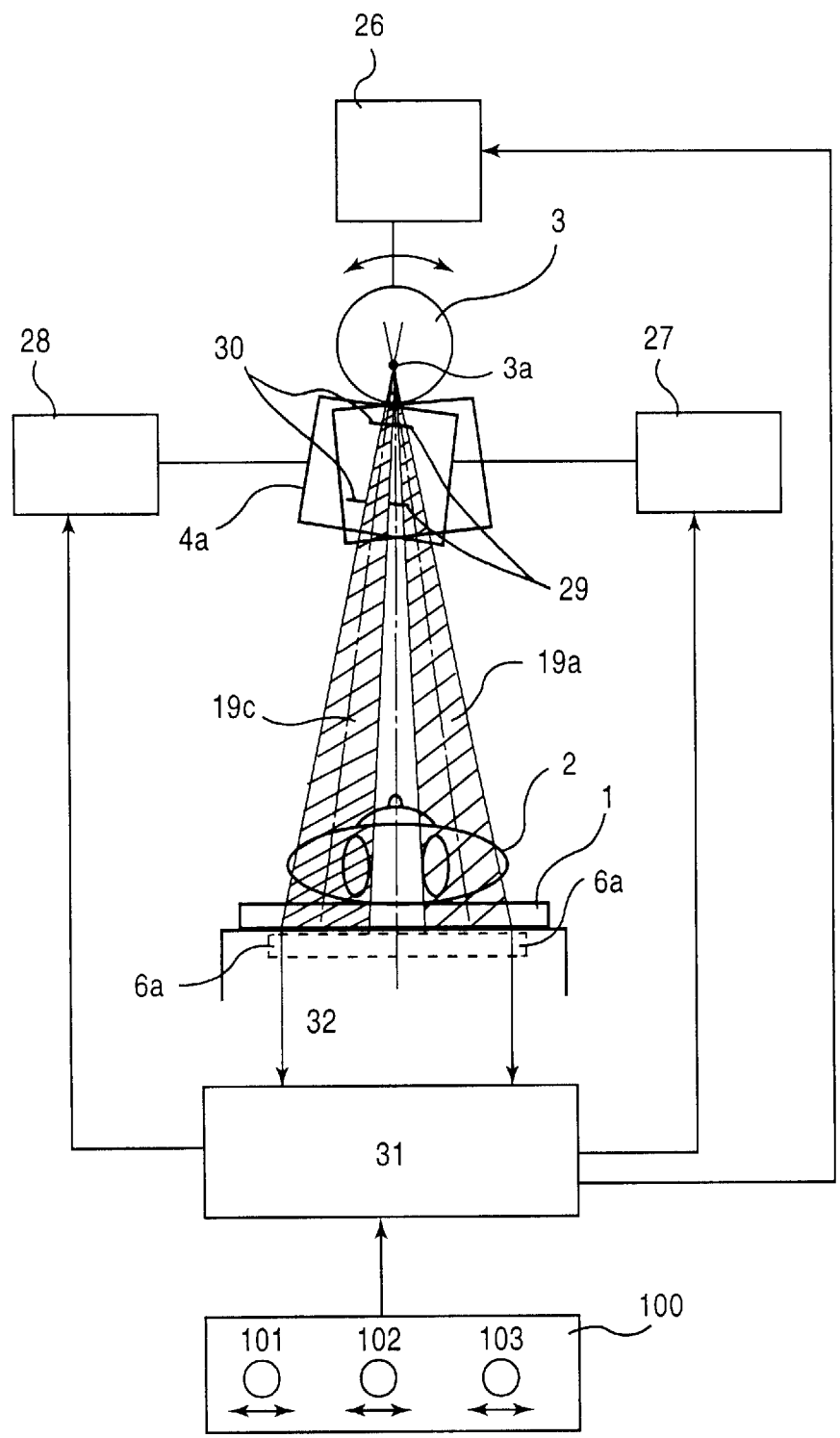
FIG. 3 is a schematic view for explanation of an operation of an X-ray apparatus in the embodiment of this invention.

The following is a detailed description of an embodiment of an X-ray apparatus of this invention, with reference of FIGS. 1–3. FIG. 1 shows a state of an X-ray flux 19a rotating about a focal point 3a of an X-ray tube 3 along a plane which is perpendicular to the body axis of a person 2. FIG. 2 is a plane view of a flat panel detector 6 with which the X-ray apparatus is equipped. FIG. 3 is a schematic view for explanation of an operation of an X-ray apparatus in the embodiment of this invention.

In FIG. 1, a supporting arm 35 supports an X-ray tube 3 and the flat panel detector 6 which oppose to each other across the person 2. A supporting base 36 supports all structures of the X-ray apparatus. An X-ray tube rotation driver 26 rotates the X-ray tube about the focal point 3a along a plane, which is perpendicular to the body axis of the person 2. The X-ray tube 3 has an aperture, through which X-rays come out, where an X-ray limiting device 4a is attached. The X-ray tube 3 rotates with the X-ray limiting device 4a. The flat panel detector 6 detects X-rays transmitted through the person 2.

In FIG. 3, a control part 31 controls the X-ray tube rotation driver 26 to rotate the X-ray tube 3 about the focal point 3a in the right and left direction. A control panel 100 has a handle 101, which is used to instruct rotation of the X-ray tube 8 through the control part 31 and the X-ray tube rotation driver 26. An operator can move the X-rays flux center 19c to the right or left target part of the person 2 by inclining a handle 101 on the control panel 100 on the control panel 100 in the right or left direction as watching a photofluorography image on a monitor. The rotation center of the X-ray tube 3 is set at the focal point 3a of the X-ray tube 3 in this embodiment. However, the rotation center may be set at a point other than the focal point 3a. One of ordinary skill in the art would appreciate that, in this embodiment; the focal point 3a is positioned on a stationary axis that is disposed above the patient and extends parallel with the patient's body axis. However, in any event, the driver rotates the X-ray tube and the X-ray limiting device about the stationary axis in an arc defining a plane oriented perpendicularly to the patient's body axis.

Figure 8:
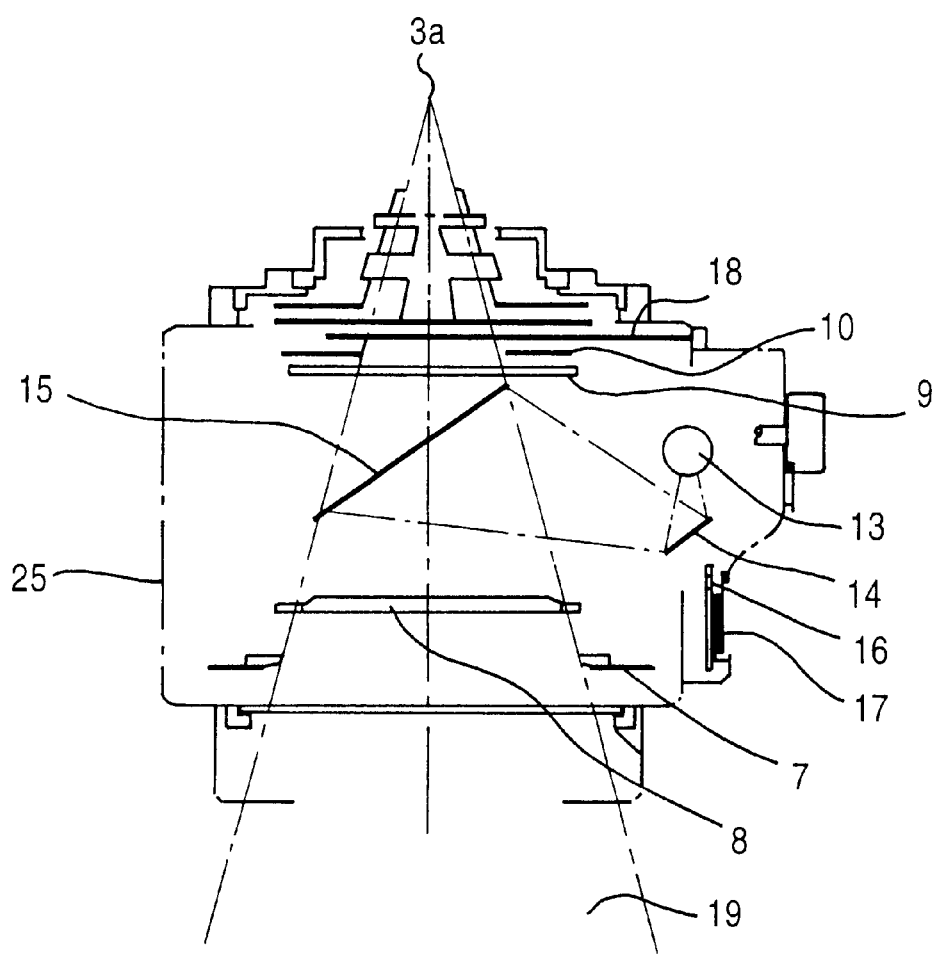
FIG. 8 is a schematic view of an X-ray limiting device.

The X-ray limiting device 4a, which is attached to the aperture of the X-ray tube 3, has R shield blades 30 corresponding to the right, blades of the lower blades 10 and upper blades 7, as shown in FIG. 8. The X-ray limiting device 4a is structured so that the R shield blades 30 and L shield blades 29 move independently from each other. A control part 31, receiving signals from the edge detector 6a, controls a R shield blade driver 28 and L shield blade driver 27 which drive the R shield blades 30 and L shield blades 29 in the X-ray limiting device 4a, respectively. The control panel 100 also has a handle 102 and a handle 103, in addition of the handle 101. The handle 102 and handle 103 are used to instruct the movement of the R shield blades 30 and L shield blades 29 through the control part 31, respectively.

As shown in FIG. 2, the flat panel detector 6 is a solid state flat plate detector on which semiconductor elements are arranged in a matrix. The flat panel detector 6 has an image detecting part 32 which is formed with an image detecting area 32a. The flat panel detector 6 also has an edge detector 6a along four edge sides thereof. When X-rays are irradiated onto the area of the edge detector 6a, the edge detector 6a detects the X-rays and outputs signals corresponding to the X-rays to the control part 31. The flat panel detector 6 may have the edge detector 6a along two edge sides thereof along the width of the person 2.

The edge detector 6a consists of the X-ray semiconductor elements in a part of four edge sides among the whole X-ray semiconductor elements on the flat panel detector 6. The edge detector 6a may also be a separate X-ray detector from the whole X-ray semi-conductor elements on the flat panel detector 6.

Figure 4:
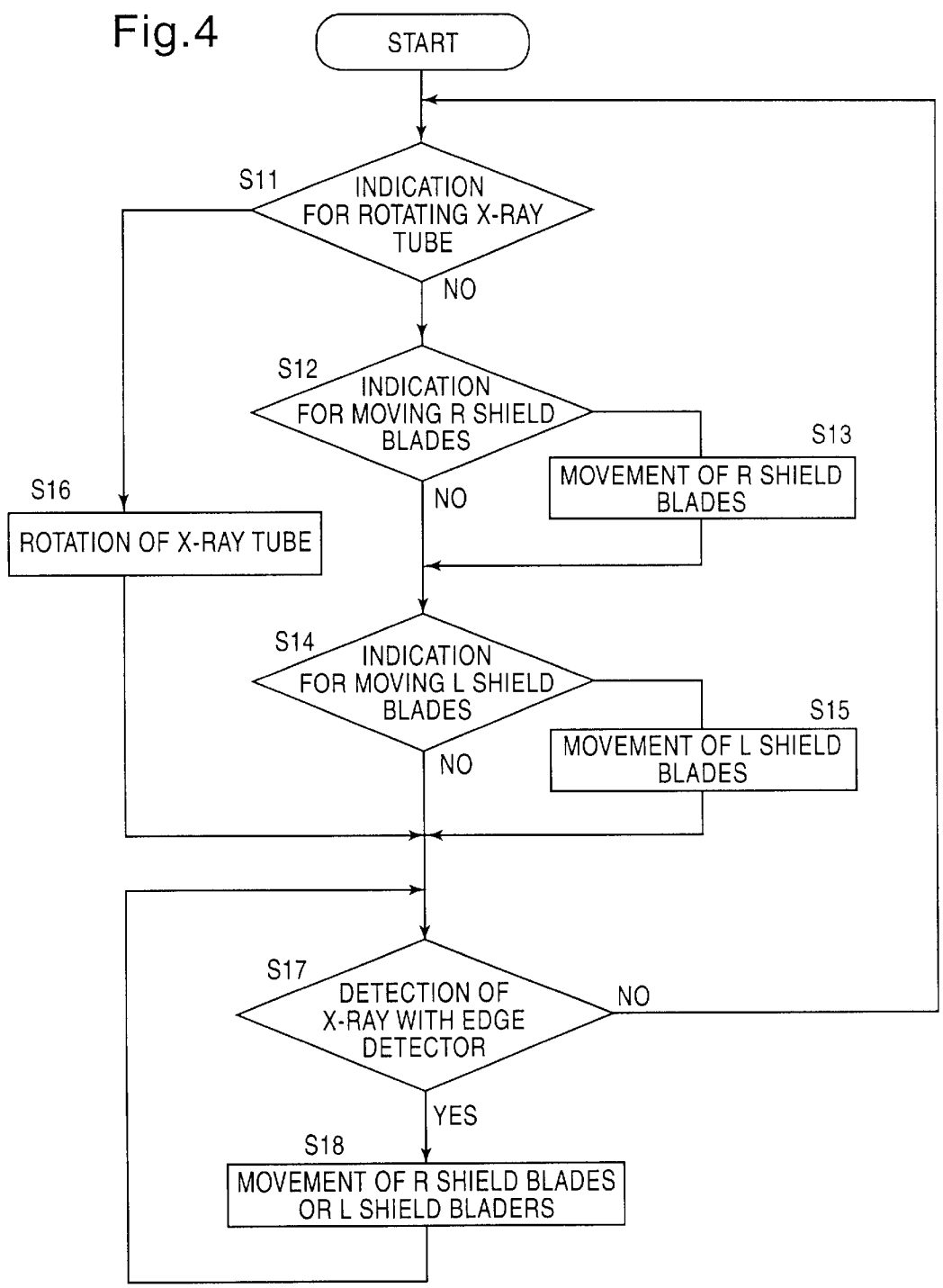
FIG. 4 is a flow diagram showing an operation of an X-ray apparatus in the embodiment of this invention.

The following is a detailed description of an operation of the embodiment, with reference of FIG. 3 and FIG. 4 with a flow diagram of operation of the control part 31. The person 2 rests on the table 1 and then a bronchoscope or endoscope is inserted in the mouth to observe the inside thereof. Then, radioscopy is performed to recognize the target part of the person 2 with the person 2 standing still. When the target part is in either of the left or right side of the person 2, the operator rotates the X-ray tube 3 by inclining the handle 101 so that the X-ray flux center 19c comes to the target part. The control part 31 controls the X-ray tube rotation driver 26 to rotate the X-ray tube 3 by the amount in proportion to the signal value provided by a sensor, not shown in the figures, which detects the amount of inclination of the handle 101.

In the above operation, as shown in the FIG. 4, first, the control part 31 monitors if there is an indication for rotating the X-ray tube 3 through the handle 101, an indication for moving the R shield blades 30 through the handle 102, and an indication for moving the L shield blades 29 through the handle 108 (S11, S12, S14). When recognizing an indication for rotating the X-ray tube 3, the control part 31 rotates, through the X-ray tube rotation driver 26, the X-ray tube 3 by the rotation amount indicated with the handle 101 (S16). Then, the control part 31 judges if the X-ray flux 19a reaches the edge detector 6a by receiving signals from the edge detector 6a (S17).

When the control part 31 judges that the X-ray flux 19a reaches the edge detector 6a, it moves either of the R shield blades 30 or L shield blades 29 by the certain amount which places in the side of the edge detector 6a which detected X-ray through the R shield blade driver 28 or L shield blade driver 27 (S18), then the control part 31 reiterates this operation until the edge detector 6a does not detect X-ray (S17, S18). When the edge detector 6a does not become to detect X-ray, the control part 31 monitors the indications from the handle 101, the handle 102, or the handle 103 again (S11, S12, S14).

The above operation makes it possible to move the center of the X-ray irradiation field without moving the body of the person and also to prevent the X-ray irradiation field from going outside of the image detecting part 32.

The operation of the handle 102 or handle 103 make it possible to move one of the R shield blades 30 or L shield blades 29 independently, for example, depending on the size of the target part (S12, S13, S14, S15).

This operation makes it possible to perform an X-ray imaging with the necessary and sufficient size of the X-ray irradiation field. In this case, since the control part 31 also judges if the edge detector 6a detects X-rays (S17), when the control part 31 judges that the edge detector 6a detects X-rays, it moves either of the R shield blades 30 or L shield blades 29, by the certain amount. This shifts the X-rays from the edge detector 6a, through the R shield blade driver 28 or L shield blade driver 27 (S18), and the control part 31 reiterates this operation until the edge detector 6a does not detect X-rays (S17, S18). Therefore, in spite of possible over operation of the handle 102 or the handle 103, the control part 31 makes it possible to prevent the X-ray irradiation field, formed by X-ray flux 19a, from going outside of the image detecting part 32.

In the above embodiment, the R shield blades 30 and the L shield blades 29 of the X-ray limiting device 4a are controlled based on signals provided by the edge detector 6a placed along the edges of the flat panel detector 6. However, it is also possible to control the R shield blades 30 and the L shield blades 29 for the X-ray irradiation field, formed by the X-ray flux 19a not to go out of the image detecting part 32 of the flat panel detector 6 by a calculation with the rotation angle of the X-ray tube 3 and the size of the X-ray irradiation field limited by the X-ray limiting device 4a.

Figure 5:
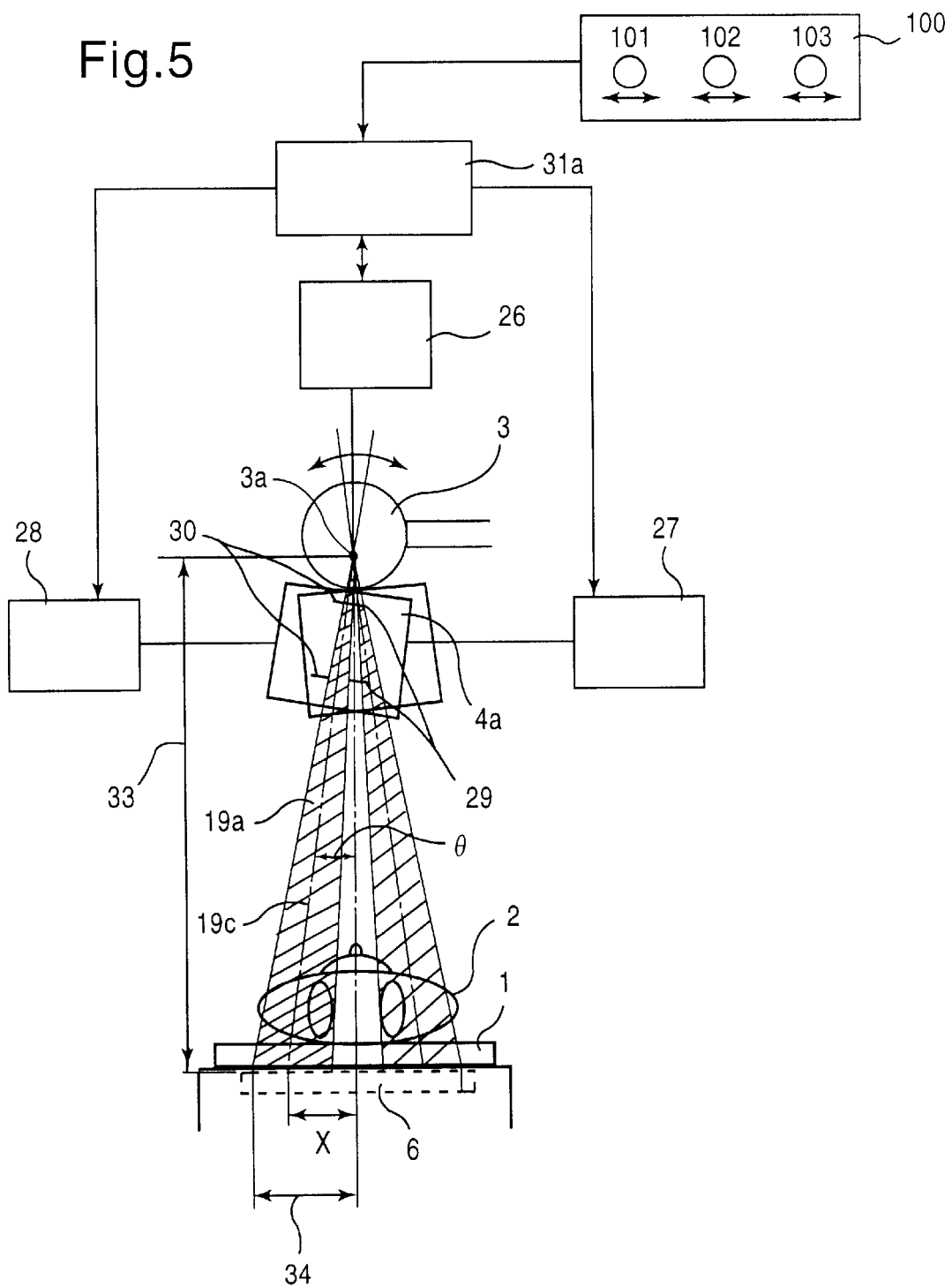
FIG. 5 is a schematic view for explanation of another operation of an X-ray apparatus in the embodiment of this invention.
Figure 6:
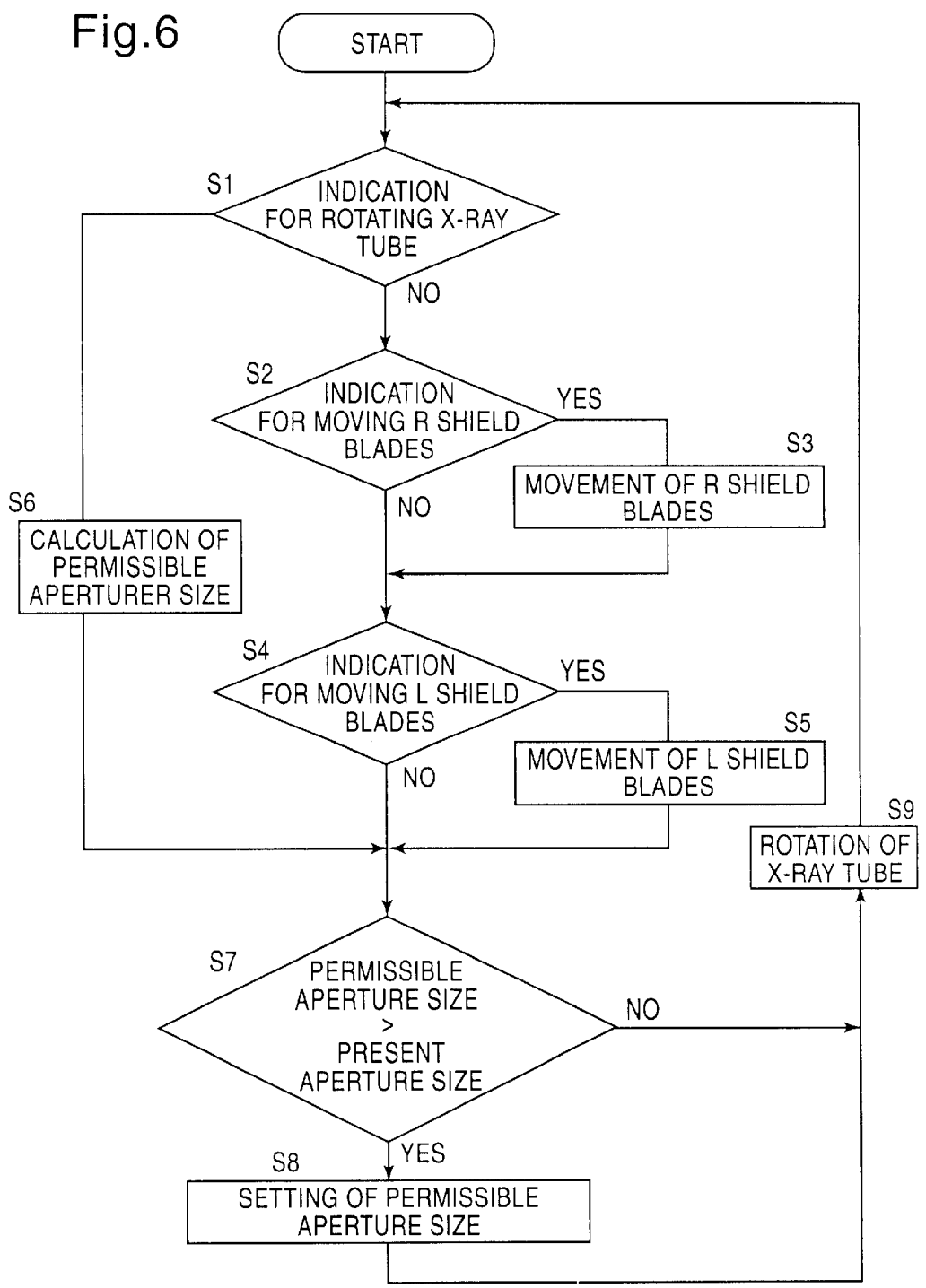
FIG. 6 is a flow diagram showing another operation of an X-ray apparatus in the second embodiment of this invention.
Figure 7:
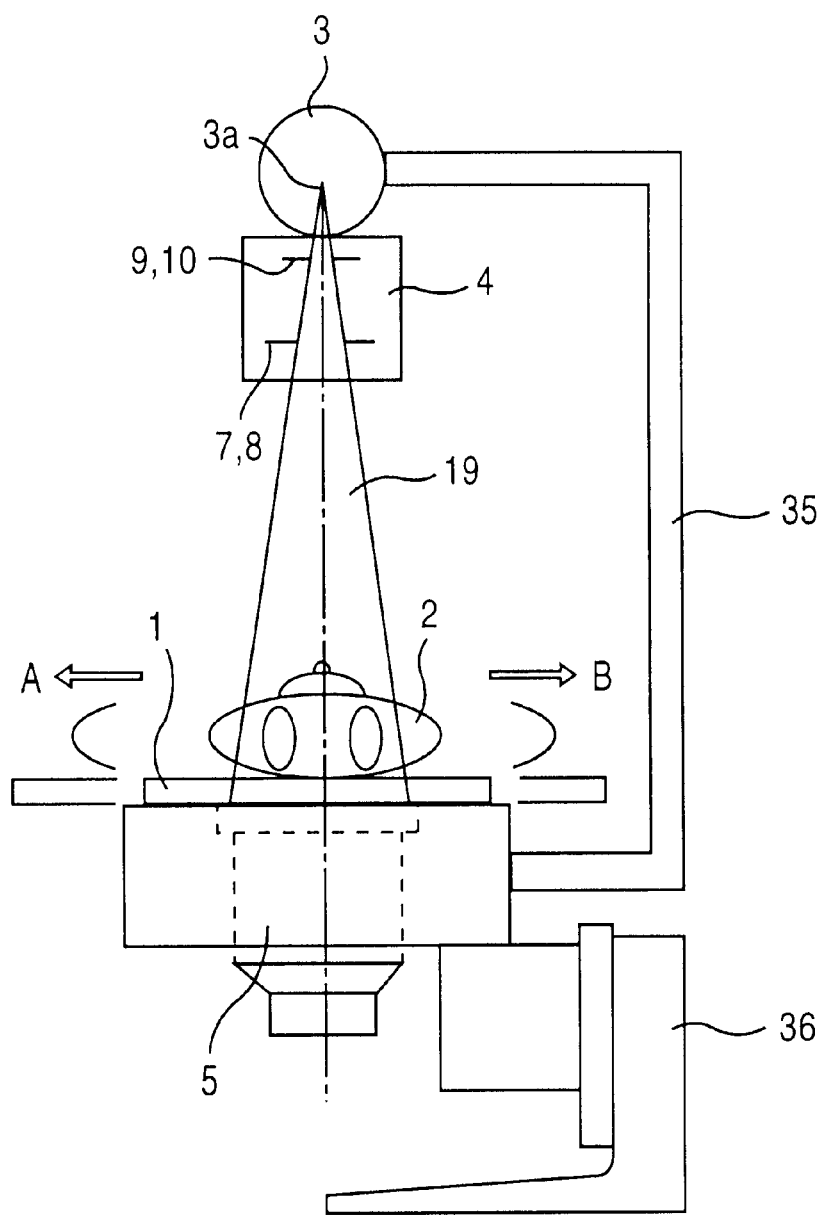
FIG. 7 is a conventional X-ray apparatus.

The following is a detailed description of an operation of this embodiment, with reference of FIG. 5 and FIG. 6 with a flow diagram of operation of the control part 31.

The control part 31 monitors if there is an indication for rotating the X-ray tube 3 through the handle 101, an indication for moving the R shield blades 30 through the handle 102, and an indication for moving the L shield blades 29 through the handle 103 (S1, S2, S4). Recognizing an indication for rotating the X-ray tube 3, the control part 31 calculates the permissible aperture size AP after rotating the X-ray tube 3 by the rotation amount indicated with the handle 101 (S6). The permissible aperture size AP is defined as the distance from the X-ray flux center 19c to the edge of the flat panel detector 6.

In FIG. 5, the permissible aperture size AP is calculated from the following formula:

$$AP = \text{the center-edge distance (34)} - X \quad (1)$$

Where $X = \{\text{the focal point–panel distance (33)}\} \times \tan \theta$

In the above formula, θ is defined as the X-ray tube rotation angle, which shows the amount of the rotation degree of the X-ray tube 3 from the center of the flat panel detector 6. X is defined as the distance from the center of the flat panel detector 6 to the x-ray flux center 19c. The center-edge distance 34 is defined as the distance from the center of the flat panel detector 6 to the edge of the image detecting part 32 of the flat panel detector 6. The focal point—panel distance 33 is defined as the distance from the focal point 3a to the center of the flat panel detector 6.

When the permissible aperture size AP is smaller than the distance, on the flat panel detector 6, of the outer half defined as the part between the outer edge of the X-ray flux 19a and the X-ray flux center 19c, the control part 31 controls the L shield blade driver 27 or the R shield blade driver 28 to move either the R shield blades 30 or the L shield blades 29, so that the distance from the X-ray flux center 19c becomes the permissible aperture size AP (S7, S8), then rotates the X-ray tube 3 by the rotation amount indicated (S9).

When the permissible aperture size AP is larger than the distance of the outer half on the flat panel detector 6, the control part 31 rotates the X-ray tube 3 by the rotation amount indicated (S7, S9). Then the control part 31 monitors the indications from the handle 101, the handle 102, or the handle 103 again (S1, S2, S4).

The R shield blades 30 and the L shield blades 29 can be controlled independently with the handle 102 and handle 103 depending on the size of the target part of the person 2, as the operation shown in FIG. 4.

In the above embodiment, the permissible aperture size AP is defined as the distance between the X-ray flux center 19c and the edge of the image detecting part 32 of the flat panel detector 6. However, the permissible aperture size may be defined as the angle from the X-ray flux center 19c to the edge of the image detecting part 32 of the flat panel detector 6. In this case, the permissible aperture size AP can be obtained with the following formula.

$$AP = \theta_F - \theta, \quad (2)$$

with $\tan \theta_F = $(the center-edge distance (34))/(the focal point—panel distance (33)).

In the embodiment shown in FIG. 3, the control part 31 receives signals from the edge detector 6a and only provides signals for controlling the R shield blade driver 28 and the L shield blade driver 27. In the embodiment shown in FIG. 5, the edge detector 6a is not needed, but the controller 31 needs a calculation function.

in the embodiments shown in FIGS. 3–6, the R shield blades 30 and the L shield blades 29 are structured to move independently with the operation of the handle 102 and the handle 103. However, the R shield blades 30 and the L shield blades 29 may be structured to move by the same distance dependently in the opposite direction from each other. This embodiment makes it possible to operate both of them with a single handle.

In the above mentioned X-ray apparatus, since an X-ray tube rotates about its focal point along a plane which is perpendicular to the body axis, X-ray irradiation field can be changed without moving the table.

Therefore, when an examination with a brouchoscope, endoscope and so on is carried out, the examination can continue without moving the person into whom the hardware is inserted.

Furthermore, in this invention, when X-rays are irradiated onto any edge area on the flat panel detector, the X-rays do not go outside of the edge of the flat panel detector. Therefore, unnecessary X-rays for imaging can be cut out.

What is claimed is:

1. An X-ray apparatus, comprising:
   an X-ray tube;
   a solid state flat detector opposing said X-ray tube across a patient being examined, the patient defining a body axis;
   an X-ray limiting device for limiting X-rays from said X-ray tube;
   a driver for rotating said X-ray tube and said X-ray limiting device about a stationary axis disposed above the patient and extending parallel to the body axis, wherein the driver rotates said X-ray tube and said X-ray limiting device in an arc defining a plane oriented perpendicularly to the body axis;
   an edge detector for detecting x-rays irradiated onto an edge part of said solid state flat detector; a controller for receiving a signal from said edge detector and controlling, with said signal, said X-ray limiting device so that X-rays do not go outside of said solid state flat detector.

2. An X-ray apparatus according to the claim 1, wherein said edge detector comprises X-ray semiconductor elements in edge parts of said solid state flat detector.

3. An X-ray apparatus according to the claim 1, wherein said edge detector comprises a separate X-ray detector from said solid state flat detector.

4. An X-ray apparatus according to the claim 1, further comprising:
   a handle for providing signals depending on an amount of manipulation set by an operator;
   an X-ray tube rotation controller for rotating said X-ray tube depending on said signals.

5. An X-ray apparatus according to the claim 1, wherein said X-ray limiting device having two shield blades which limit X-rays in a direction which is perpendicular to a body axis of said person.

6. An X-ray apparatus according to the claim 5, further comprising:
   a handle for providing signals depending on an amount of manipulation set by an operator;
   a shield blade movement controller for moving said two shield blades in opposite directions from each other, depending on said signals.

7. An X-ray apparatus according to the claim 5, further comprising:
   two handles for providing signals depending on amounts of manipulation set by an operator;
   a shield blade movement controller for moving said two shield blades independently, depending on said signals.

8. An X-ray apparatus according to the claim 1, further comprising:
   a detector for detecting a rotation angle of said X-ray tube, and providing a signal related to said rotation angle;
   a controller for receiving said signal from said detector and controlling said X-ray limiting device so that X-rays from said X-ray tube do not go outside of said solid state flat detector.

9. An X-ray apparatus according to claim 1, wherein the X-ray tube and the X-ray limiting device are connected to each other.

10. An X-ray apparatus according to claim 9, wherein the X-ray tube and the X-ray limiting device are simultaneously rotated by the driver about the arc.

11. An X-ray apparatus, comprising:
    an X-ray tube;
    a solid state flat detector opposing said X-ray tube across a patient being examined, the patient defining a body axis;
    an X-ray limiting device for limiting X-rays from said X-ray tube;
    a driver for rotating said X-ray tube and said X-ray limiting device about a stationary axis disposed above the patient and extending parallel to the body axis in an arc defining a plane oriented perpendicularly to the body axis;
    a detector for detecting a rotation angle of said X-ray tube, and providing a signal related to said rotation angle; and
    a controller for receiving said signal from said detector and controlling said X-ray limiting device so that X-rays from said X-ray tube do not go outside of said solid state flat detector,
    wherein said controller calculates a permissible aperture size defined as a distance between a center of an X-ray irradiation field and an edge of said solid state flat detector, and controlling said X-ray limiting device so that an outer half of X-rays from said X-ray tube is limited to within said permissible aperture size.

12. An X-ray apparatus according to the claim 11, wherein said X-ray limiting device has two shield blades which move along a plane which is perpendicular to a body axis, said blades limiting the X-rays.

13. An X-ray apparatus according to the claim 12, further comprising:
    a handle for providing signals depending on an amount of manipulation set by an operator;
    a shield blade movement controller for moving the two shield blades in opposite directions from each other, depending on said signals.

14. An X-ray apparatus according to the claim 11, further comprising:
    two handles for providing signals depending on amounts of manipulation set by an operator;
    a shield blade movement controller for moving two shield blades independently, depending on said signals.

15. An X-ray apparatus, comprising:
    an X-ray tube;
    a solid state flat detector opposing said X-ray tube across a patient being examined, the patient defining a body axis;
    an X-ray limiting device for limiting X-rays from said X-ray tube;
    a driver for rotating said X-ray tube and said X-ray limiting device about a stationary axis disposed above the patient and extending parallel to the body axis in an arc defining a plane oriented perpendicularly to the body axis;
    a detector for detecting a rotation angle of said X-ray tube, and providing a signal related to said rotation angle; and
    a controller for receiving said signal from said detector and controlling said X-ray limiting device so that X-rays from said X-ray tube do not go outside of said solid state flat detector,
    wherein said controller calculates a permissible aperture size based on an angle between an edge of said solid state flat plate detector and a center of an X-ray irradiation field, and controlling said X-ray limiting device so that an outer half of X-rays from said X-ray tube is limited to within said permissible aperture size.

* * * * *